United States Patent
Hefti et al.

(10) Patent No.: US 7,083,985 B2
(45) Date of Patent: Aug. 1, 2006

(54) COPLANAR WAVEGUIDE BIOSENSOR FOR DETECTING MOLECULAR OR CELLULAR EVENTS

(76) Inventors: John J. Hefti, 21 Escondido Ave., San Francisco, CA (US) 94132; Barrett Bartell, 34 Kings Canyon Way, Pacifica, CA (US) 94044; Kurt Kramer, 1070 Kains Ave., Apt. No. 3, Albany, CA (US) 94706; Mark A. Rhodes, 735 Sapphire St., Redwood City, CA (US) 94061

( * ) Notice: Subject to any disclaimer, the term of this patent is extended or adjusted under 35 U.S.C. 154(b) by 674 days.

(21) Appl. No.: 10/226,794

(22) Filed: Aug. 23, 2002

(65) Prior Publication Data

US 2003/0040004 A1 Feb. 27, 2003

Related U.S. Application Data

(63) Continuation-in-part of application No. 09/929,521, filed on Aug. 13, 2001, now abandoned, which is a continuation-in-part of application No. 09/365,978, filed on Aug. 2, 1999, now Pat. No. 6,485,905, which is a continuation-in-part of application No. 09/243,194, filed on Feb. 1, 1999, now Pat. No. 6,368,795.

(60) Provisional application No. 60/073,445, filed on Feb. 2, 1998.

(51) Int. Cl.
    *G01N 33/543* (2006.01)
(52) U.S. Cl. ............... 436/518; 385/4; 385/8; 385/9; 385/12; 385/129; 422/82.01; 435/6; 435/7.1; 435/7.92; 435/287.1; 435/287.2; 436/149; 436/150; 436/151; 436/517; 436/524; 436/525; 436/805; 436/806

(58) Field of Classification Search ............ 435/6, 435/7.1, 7.92, 287.1, 287.2; 436/149, 150, 436/151, 517, 518, 524, 525, 805, 806; 422/82.01; 385/4, 8, 9, 12, 129

See application file for complete search history.

(56) References Cited

U.S. PATENT DOCUMENTS

| 5,187,096 | A   |   | 2/1993  | Giaever et al. | 435/291 |
| 5,846,708 | A   |   | 12/1998 | Hollis et al.  | 435/6   |
| 5,989,402 | A   |   | 11/1999 | Chow et al.    | 204/601 |
| 6,287,874 | B1  | * | 9/2001  | Hefti          | 436/501 |
| 6,338,968 | B1  | * | 1/2002  | Hefti          | 436/518 |
| 6,376,258 | B1  | * | 4/2002  | Hefti          | 436/518 |
| 6,395,480 | B1  | * | 5/2002  | Hefti          | 435/6   |
| 6,485,905 | B1  | * | 11/2002 | Hefti          | 435/6   |

FOREIGN PATENT DOCUMENTS

| DE | 199 16 867 A | 10/2000 |
| EP | 0519250 A2   | 12/1992 |

OTHER PUBLICATIONS

Hefti et al., "Sensitive Detection Method of Dielectric Dispersions in Aqueous-Based, Surface-Bound Macromolecular Structures Using Microwave Spectroscopy" Applied Physics Letters, American Institute of Physics. New York, US, vol. 75, No. 12, pp. 1802-1804 (1999).

* cited by examiner

*Primary Examiner*—Christopher L. Chin
(74) *Attorney, Agent, or Firm*—Kelvan P. Howard; Richard Neeley

(57) ABSTRACT

A coplanar waveguide biosensor and methods of use include a coplanar waveguide transmission line and a sample containment structure. The coplanar waveguide transmission line is operable to support the propagation of an electromagnetic signal and includes a signal line and one or more spaced apart ground elements. The signal line is configured to conduct a time-varying voltage, and the one or more ground elements are configured to maintain a time-invariant voltage, a detection region being formed between a portion of the signal line and a portion of at least one of the one or more ground elements. Detection methods are improved through the enhancement of the electric field in the detection region via impedance discontinuities in the signal line and ground elements. The sample containment structure intersects the detection region of the coplanar waveguide transmission line and includes a cavity configured to hold 1 ml or less of sample solution within the detection region.

25 Claims, 7 Drawing Sheets

COPLANAR WAVEGUIDE BIOSENSOR FOR DETECTING MOLECULAR OR CELLULAR EVENTS

CROSS REFERENCE TO RELATED APPLICATIONS

This patent application is a continuation-in-part of U.S. patent application Ser. No. 09/929,521 filed Aug. 13, 2001 now abandoned, which is a continuation-in-part of application Ser. No. 09/365,978 now U.S. Pat. No. 6,485,905, filed Aug. 2, 1999 and issued Nov. 26, 2002, which is a continuation-in-part of application Ser. No. 09/243,194 U.S. Pat. No. 6,368,795, filed Feb. 1, 1999 and issued Apr. 9, 2002, which claims the benefit of U.S. Provisional application No. 60/073,445, filed Feb. 2, 1998 and now abandoned.

BACKGROUND OF THE INVENTION

The present invention relates to biosensors and more particularly to coplanar waveguide biosensors configured to detect molecular or cellular events.

A number of bioelectric sensors are known in the biotechnical arts and use electronic signals to detect and identify the structure and interactions of molecules, as well as cellular function and activity. In the past, bioelectric sensors ("biosensors") typically have been constructed in a parallel-plate capacitor device in which layers of probes are immobilized on of the opposing surfaces between the capacitor plates. The sought targets have a high binding affinity for the probes and, when captured onto the plate surface, operate to change the capacitance of the biosensor. The change in capacitance can be measured by passing an electronic signal (typically a time-varying ac signal of relatively low frequency) between the two capacitor plates before and after binding and comparing the respective responses. Examples of these types of biosensors are disclosed in U.S. Pat. No. 5,653,939 to Hollis et al., as well as U.S. Pat. No. 5,187,096 to Giaever et al. which discloses a similar structure for cell-based measurements.

The capacitor-type biosensor suffers from some disadvantages, one being the relatively low frequency range over which the biosensor can be used. Typically, the measured cells or molecules situated between the plates will reside in an aqueous environment which significantly attenuates signals propagating between the two plates. As a result, the highest frequency signal measurements are typically in the high KHz region to low MHz. As recent developments in the laboratories of the present inventors have demonstrated, a significant amount of information can be obtained by interrogating molecular and cellular activity at both these commonly used frequencies and at higher frequencies. An improved biosensor capable of operation over a broader range of frequencies would therefore be advantageous.

SUMMARY OF THE INVENTION

The present invention provides a broadband coplanar waveguide biosensor for detecting molecular or cellular events. In one embodiment, the coplanar waveguide biosensor includes a one-port coplanar waveguide transmission line and a sample containment structure. The one-port coplanar waveguide transmission line is operable to support the propagation of an electromagnetic signal and includes a signal line and one or more spaced-apart ground elements. The signal line is configured to conduct a time-varying voltage, and the one or more ground elements are configured to maintain a time-invariant voltage, a detection region being formed between a portion of the signal line and a portion of at least one of the one or more ground elements. The sample containment structure intersects the detection region of the one-port coplanar waveguide transmission line and includes a cavity configured to hold 1 ml or less of sample solution within the detection region. The coplanar waveguide architecture of the described biosensor enables operation at frequencies higher than previously presented.

The present invention will be better understood in light of the following drawings and detailed description.

BRIEF DESCRIPTION OF THE DRAWINGS

For convenience and clarity, like numerals identify like parts throughout the drawings.

DESCRIPTION OF THE SPECIFIC EMBODIMENTS

Definitions

Figure 1A:
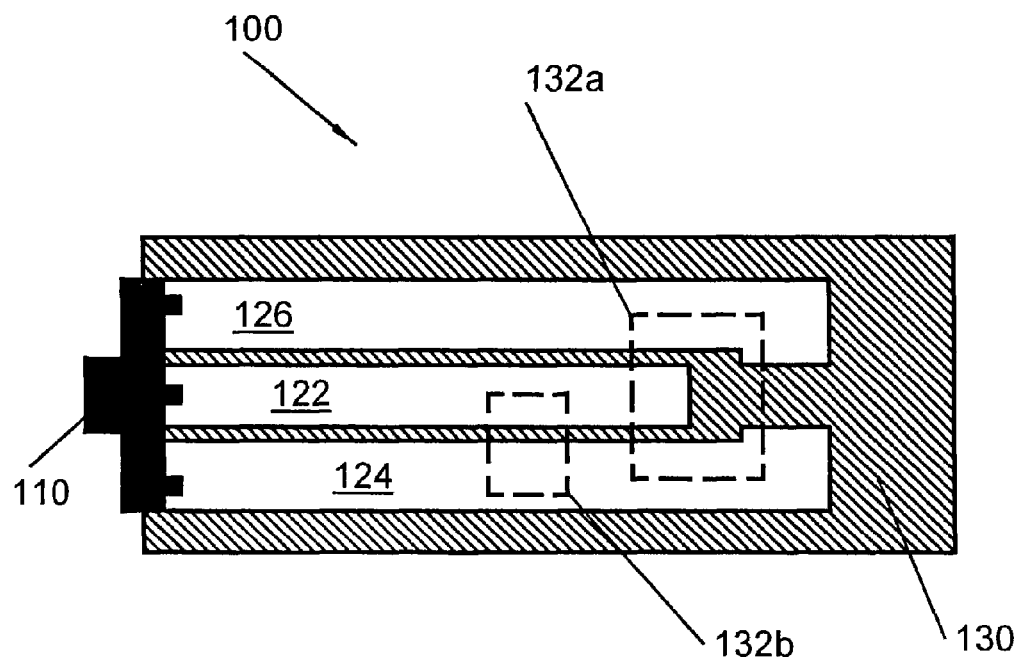
FIG. 1A illustrates top view of a first embodiment of the coplanar waveguide biosensor in accordance with the present invention.

As used herein, the term "molecular event" refers to the interaction of a molecule of interest with another molecule (e.g., molecular binding) and to all structural properties of molecules of interest. Structural molecular properties include the presence of specific molecular substructures (such as alpha helix regions, beta sheets, immunoglobulin domains, and other types of molecular substructures), as well as how the molecule changes its overall physical structure via interaction with other molecules (such as by bending or folding motions), including the molecule's interaction with its own solvation shell while in solution. The simple presence of a molecule of interest in the region where detection/analysis is taking place is not considered to be a "molecular event," but is referred to as a "presence."

Examples of molecular binding events are (1) simple, non-covalent binding, such as occurs between a ligand and its antiligand, and (2) temporary covalent bond formation, such as often occurs when an enzyme is reacting with its substrate. More specific examples of binding events of interest include, but are not limited to, ligand/receptor, antigen/antibody, enzyme/substrate, DNA/DNA, DNA/RNA, RNA/RNA, nucleic acid mismatches, complementary nucleic acids and nucleic acid/proteins. Binding events can occur as primary, secondary, or higher order binding events. A primary binding event is defined as a first molecule binding (specifically or non-specifically) to an entity of any type, whether an independent molecule or a material that is part of a first surface, typically a surface within the detection region, to form a first molecular interaction complex. A secondary binding event is defined as a second molecule binding (specifically or non-specifically) to the first molecular interaction complex. A tertiary binding event is defined as a third molecule binding (specifically or non-specifically) to the second molecular interaction complex, and so on for higher order binding events.

Examples of relevant molecular structures are the presence of a physical substructure (e.g., presence of an alpha helix, a beta sheet, a catalytic active site, a binding region, or a seven-trans-membrane protein structure in a molecule) or a structure relating to some functional capability (e.g., ability to function as an antibody, to transport a particular ligand, to function as an ion channel (or component thereof), or to function as a signal transducer). Molecular structure is typically detected by comparing the signal obtained from a molecule of unknown structure and/or function to the signal obtained from a molecule of known structure and/or function. Molecular binding events are typically detected by comparing the signal obtained from a sample containing one of the potential binding partners (or the signals from two individual samples, each containing one of the potential binding partners) to the signal obtained from a sample containing both potential binding partners.

The term "cellular event" refers in a similar manner to reactions and structural rearrangements occurring as a result of the activity of a living cell (which includes cell death). Examples of cellular events include opening and closing of ion channels, leakage of cell contents, passage of material across a membrane (whether by passive or active transport), activation and inactivation of cellular processes, as well as all other functions of living cells. Cellular events are commonly detected by comparing modulated signals obtained from two cells (or collection of cells) that differ in some fashion, for example by being in different environments (e.g., the effect of heat or an added cell stimulant) or that have different genetic structures (e.g., a normal versus a mutated or genetically modified cell). Morpholic changes are also cellular events. Other examples of cellular events are illustrated in applicant's concurrently filed application entitled "Methods for Analyzing Cellular Events," Ser. No. 09/929,513 herein incorporated by reference in its entirety for all purposes.

The same bioassay systems can be used for molecular and cellular events, differing only in the biological needs of the cells versus the molecules being tested. Accordingly, this specification often refers simply to "events" for simplicity, in order to avoid the awkwardness of continually referring to "molecular and/or cellular" events, detection, sample handling, etc., when referring to an apparatus that can be used to detect either molecular events or cellular events. When appropriate for discussion of a particular event, the event will be described as, for example, a cellular event, a molecular binding event, or a molecular structure determination.

When a molecular event (e.g., binding of a potential drug with, a receptor) is being detected in a biological sample capable of undergoing biological functions (e.g., a cell or a cell-free enzyme system), the molecular event can be amplified by the biological function and, if desired to increase sensitivity, the change resulting from the function can be detected rather than the molecular event itself. Examples of detectable amplified signals include the permittivity change of a cell resulting from the opening or closing of an ion channel when a molecular binding event occurs and a physiological reaction (e.g., synthesis of a protein) of a cell when a drug interacts with a cellular receptor. When working with cells, such binding event detection can be referred to as detection of a "cellular molecular event" (as opposed to a "non-cellular molecular event," which is one that occurs in the absence of cells). Similar language can be used to describe cell-free enzyme-system molecular events.

As used herein, the term "sample solution" refers to the material being investigated (the biological sample, defined below) and the medium/buffer in which the analyte is found. The medium or buffer can included solid, liquid or gaseous phase materials; the principal component of most physiological media/buffers is water. Solid phase media can be comprised of naturally occurring or synthetic molecules including carbohydrates, proteins, oligonucleotides, $SiO_2$, GaAs, Au, or alternatively, any organic polymeric material, such as Nylon®, Rayon®, Dacryon®, polypropylene, Teflon®, neoprene, delrin or the like. Liquid phase media include those containing an aqueous, organic or other primary components, gels, gases, and emulsions. Exemplary media include celluloses, dextran derivatives, aqueous solution of d-PBS, Tris, deionized water, blood, cerebrospinal fluid, urine, saliva, water, and organic solvents.

As used herein, a "biological sample" is a sample of biological tissue or fluid that, in a healthy and/or pathological state, is to be assayed for the structure(s) or event(s) of interest. Such biological samples include, but are not limited to, sputum, amniotic fluid, blood, blood cells (e.g., white cells), tissue or fine needle biopsy samples, urine, peritoneal fluid, pleural fluid, and cells from any of these sources. Biological samples also include cells grown in cultures, both mammalian and others. Biological-samples further include sections of tissues such as frozen sections taken for histological purposes. Although a biological sample is often taken from a human patient, the meaning is not so limited. The same assays can be used to detect a molecular event of interest in samples from any mammal, such as dogs, cats, sheep, cattle, and pigs, as well as samples from other animal species (e.g., birds, such as chickens or turkey) and plants (e.g., ornamental plants and plants used as foods, such as corn or wheat). The biological sample can be pretreated as necessary by dilution in an appropriate transporting medium solution or concentrated, if desired, and is still referred to as a "biological sample." Any of a number of standard aqueous transporting medium solutions, employing one of a variety of transporting media, such as phosphate, Tris, or the like, preferably at physiological pH can be used. As with biological samples, pretreatment of a more general sample (by dilution, extraction, etc.) once it is obtained from a source material do not prevent the material from being referred to as a sample.

As used herein, the term "test signal" refers to a sub-optical, time-varying electromagnetic signal below 1000 GHz. A preferred operating frequency range is from 10 KHz to 10 GHz, a more particularly from 100 KHz to 20 KHz. "Test signal" can refer to a range of frequencies rather than a single frequency, and such a range can be selected over any terminal frequencies, including frequency ranges bounded by the specific frequencies named in this paragraph. When referring to the detected range (or multiple) of modulated signals obtained after a range of frequencies has been coupled to a sample solution, the term "spectrum" is sometimes used. An "incident test signal" is a test signal that originates from the signal source and is destined for the detection region for interaction with the sample solution. A "modulated test signal" is a test signal that has previously interacted with the sample solution and is destined for a signal detector that can recover the modulation imparted by the signal interaction with the sample solution.

As used herein, the term "electromagnetically coupled" refers to the transfer of electromagnetic energy between two objects, e.g., the signal transmission structure and molecular events occurring within the sample solution. The two objects can be electromagnetically coupled when the objects are in direct or indirect physical contact, (e.g., molecular events attached along the surface of the signal line or on a physical intervening layer or structure), or when the objects are physically separated from each other (e.g., molecular events suspended within solution flowing through a flow tube, the flow tube positioned within the detection region). As a modification, the term "electromagnetically couples" will indicate the interaction of an electromagnetic signal (e.g., the incident test signal) with an object (e.g., molecular or cellular events occurring within the sample solution).

As used herein, the term "sample containment structure" refers to a structure having an partially or fully enclosed cavity configured to retain a predefined volume of sample, preferably less than 1 ml over a predefined area. In specific embodiments, the sample containment structure includes a well structure such as those illustrated in applicant's concurrently filed application entitled "Well-Based Biosensors for Detecting Molecular and Cellular Events," Ser. No. 09/929,520. In another embodiment, the sample containment structure consists of a fluid channel or flow tube such as those disclosed in applicant's co-pending patent application Ser. No. 09/687,456, entitled System and Method for Detecting and Identifying Molecular Events in a Test Sample,". Other similar structures will be apparent to those of skill in the art of fluidics and biosensor design.

As used herein, the term "detection region" refers to a cross-sectional volume of the coplanar waveguide transmission line through which the electromagnetic fields of a propagated test signal extend. The detection region is located between a portion of the signal line and a portion of at least one of the one or more ground elements, and extends perpendicularly to (above or below) the coplanar waveguide transmission line for a redefined distance, typically between $10^{-10}$ to $10^{-2}$ m.

The sample containment structure will intersect the detection region in various ways, depending upon the type of structure used For instance when a well structure is used as the sample containment structure, the well will hold the sample solution in physical contact with portions of the coplanar waveguide transmission line. In another embodiment a flow tube (positioned above or below the coplanar waveguide transmission line) is used as the sample containment structure and is positioned to hold the sample solution within the detection region. In this case, the sample solution does not into direct contact with portions of the coplanar waveguide transmission line. Instead, the test signal electromagnetically couples through the outer diameter of the flow tube and interacts with the molecular or cellular events occurring within the flow tube's cavity. Other sample containment structures such as fluid channels may also be used in one of these manners.

Biosensor Embodiments

FIG. 1A illustrates top view of a first embodiment of the coplanar waveguide biosensor 100 in accordance with the present invention. The biosensor 100 includes a coplanar waveguide transmission line 120 (referred to as a "cpw line") in a one port configuration, the cpw line 120 comprised of a signal line 122 located between two ground elements 124 and 126 all of which are electrically coupled to a connector 110. The signal line 122 and ground elements 124 and 126 are formed on a dielectric substrate 130, which may consist of a variety of relatively low loss electrically insulating materials such as glass, fused silica, diamond, beryllium, sapphire, polyimide, alumina, quartz, silicon dioxide, gallium arsenide, woven dielectrics, or other similar materials. The signal line 122 and the ground elements 124 and 126 can be formed from a number of compounds using a variety of deposition techniques. In a specific embodiment, the dielectric substrate 130 is composed of borosilicate glass ($\epsilon_r \approx 4.6$), the signal line 122 and ground elements 124 and 126 are composed of 1.5 um gold deposited on top of 100–200 Å titanium adhesion layer. The width of the signal line 122 and lateral separation from the ground elements 124 and 126 is usually determined by the desired characteristic impedance of the cpw line 120 and the dielectric constant of the substrate 130 onto which the lines are formed. In a particular embodiment, the desired characteristic impedance of the cpw line 120 is 50 ohms and the substrate 130 is composed of borosilicate glass ($\epsilon_r \approx 4.6$), thereby setting the width of the signal line 122 to 0.310 mm and the lateral separation from the ground elements 124 and 126 to 0.038 mm. The reader will appreciate that the invention is not limited to the foregoing specifics, and variations of in materials, desired characteristic line impedance, and line width and gap dimensions may be employed in alternative embodiments under the present invention.

In one embodiment as shown, the cpw line 120 is terminated in an open circuit, although other terminations may be used. For instance, a short circuit in which the signal line 122 and one or more of the ground elements 124 and 126 connect is possible. In another embodiment, the cpw line 120 may terminate in a load, for instance a 50 ohm standard load. In still another embodiment, the cpw line may terminate in a resonant circuit or cavity. Other terminations using active or passive components (capacitors/inductors or transistors) may be used in alternative embodiments under the present invention.

The biosensor 130 further includes a detection region 132 which intersects the signal line 122 and at least one of the ground elements 124 and 126. The detection region 132 extends perpendicular to the plane of the cpw line (above or below) a predefined distance, typically $10^{-2}$ to $10^{-10}$ m, this distance representing the distance over which electromagnetic fields (corresponding to a propagating test signal) flow above and below the cpw line 120. These fields enable electromagnetic coupling to, and accordingly detection of molecular or cellular events occurring in sample containment structures (e.g. flow tubes) that physically separate the surface of the cpw line 120 from the sample solution.

In a specific embodiment, a detection region 132a is formed around the area having the highest electromagnetic field density which typically occurring where the signal line 122 and one or more of the ground elements 124 and 126 are the most proximate. In another embodiment, the detection region 132b is formed in another location between the signal line 122 and one (or both) of the ground elements 124. In either embodiment, the detection region 132 may extend above or below the plane of the cpw line 120. Other detection regions which interest the signal line 122 and at least one of the ground elements 124 or 126 are possible under alternative embodiments of the present invention.

The biosensor 130 is operable to detect molecular or cellular events in solution, suspension, and in contact with the surface of the cpw line 120. Solution and suspension-phase detection is accomplished by propagating an incident test signal (at one or more frequencies) along the cpw line 120 to the detection region which is intersected by a sample containment structure (e.g., flow tube, flow cell, enclosed fluid channel, or the like) in which the sample solution is contained. A portion of the incident test signal electromagnetically couples through the intervening wall or layer of the sample containment structure (which is preferably made of a low dielectric loss material, such as polytetrafluoroethylene, polycarbonate, and the like) and to the event occurring in solution or suspension, the event modulating one or more characteristics (the amplitude, phase, frequency, group delay, etc.) of the incident test signal. The resulting modulated signal is recoverable through a reflection (known as "$S_{11}$" or "return loss") measurement known in the art of high frequency circuit analysis. The imparted modulation (e.g., the change in the incident signal's amplitude, phase, frequency, group delay, etc.) is indicative of the presence and identity of the event occurring within the sample solution. The distance over which the test signal can travel between the cpw line 120 and the event will typically range from $10^{-10}$ m to $10^{-2}$ m (or anywhere therebetween), depending upon such factors as the composition of the sample solution, event concentration within the sample solution, amplitude and frequency of the test signal, length of the cpw line 120, sensitivity of the signal detector, composition and thickness of intervening physical structures or linker layers, and the desired detection time.

In solid phase detection, the molecular or cellular event is physically attached (directly, or indirectly through intervening layers or linkers) to the cpw line. The sample containment structure (e.g., a well structure, open fluid channel, and the like) supplies the sample solution to the detection region where an event in the solution contacts (directly or indirectly) the signal line, the ground elements, or both structures. During testing, an incident test signal travels along the cpw line to the detection region where it electromagnetically couples to the event. The event modulates a property (as described above) of the incident test signal and the imparted modulation is recoverable by a return loss measurement. The modulation can be used as an identifier for each event, as each molecular or cellular event imparts a unique modulation to the test signal at one or more frequencies. Selective patterning of the dielectric substrate 130 with a polymer may be used to change the hydrophobicity or hydrophilicity of the surface in order to position sample solutions in the area of high electromagnetic field strength.

Figure 1B:
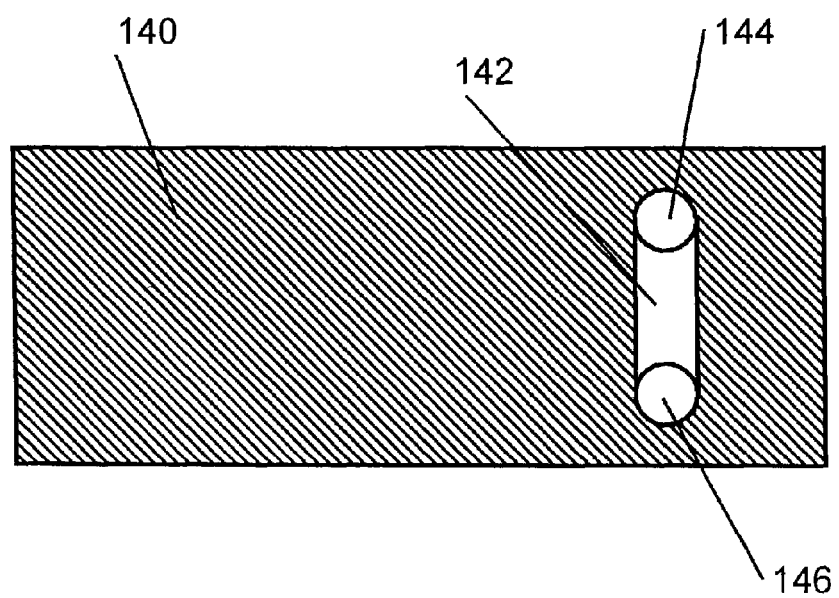
FIG. 1B illustrates a bottom view of a sample containment structure of the coplanar waveguide biosensor illustrated in FIG. 1A.

FIG. 1B illustrates a bottom view of a sample containment structure 140 for use with the biosensor illustrated in FIG. 1A. As shown, the sample containment structure 140 consists of a cavity 142 consisting, in one embodiment, of an open fluid channel disposed along the structure's bottom surface, a sample inlet port 144, and a sample outlet port 146. The fluid channel 142 is open on the illustrated bottom surface to enable the sample solution to come in to direct or indirect physical contact with portions of the cpw line 120. The fluid channel 142 is sealed (preferably water-tight) over the detection region 132 using conventional attachment techniques sized. Sample inlet and outlet ports 144 and 146 operate to supply and extract sample to and from the biosensor 100. Preferably, the fluid channel 142 of the sample containment structure is configured to contain a small volume, on the order of 1 ml or less, although a larger amount of sample may be contained within the whole of the sample containment structure itself (i.e., the total volume of sample solution contained along flow route may exceed 1 ml). In specific embodiment, the sample containment structure 140 is constructed from borosilicate glass which is wet chemical etched to form the fluid channel 142 and ports 144 and 146.

Alternatively to the foregoing example in which the molecular or cellular event is physically attached to portions of the signal line 122 and/or the ground elements 124 and/or 126, the event may be located with the separation gap between the signal line 122 and the ground elements 124 and 126. Further alternatively, the event may be immobilized on an intervening layer, such as a passivation layer or linker group. In a solution phase measurement, the sample may also come into direct or indirect (e.g., through a passivation layer) contact with the cpw line 120, although the molecular or cellular event itself will be in solution or suspension. The open fluid channel 142 or a well structure (not shown) may be used to provide this capability. In another solution phase arrangement, the sample solution is separated from the cpw line 120 through the outer wall of a flow tube or enclosed fluid channel routed through the detection region 132. Molecular and cellular events occurring in solution or suspension become detectable as they travel into or occur within the detection region 132.

Figure 2:
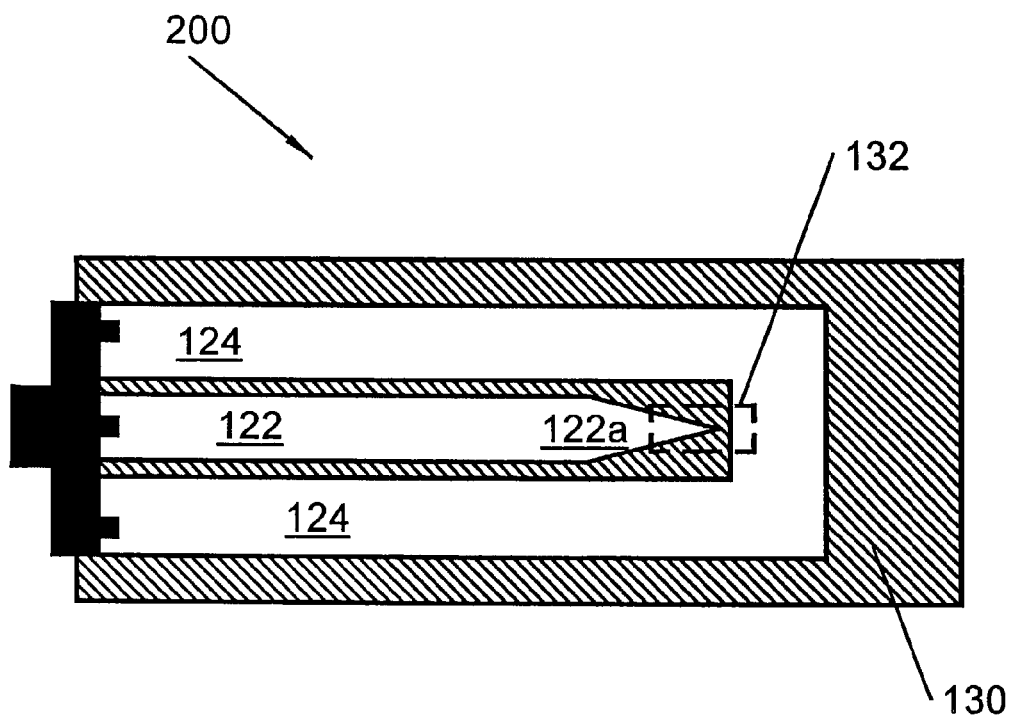
FIG. 2 illustrates a top view of a second embodiment of the coplanar waveguide biosensor in accordance with the present invention.

FIG. 2 illustrates top view of a second embodiment of the coplanar waveguide biosensor 200 in accordance with the present invention. In this embodiment, the signal line 122 includes a tapered section 122a which terminates in a sharp point proximate to a ground element 124 that extends around the signal line 122. The detection region 132 is formed over the area where the tapered point of the signal line 122 most closely approaches the ground element 124. When a signal is propagated along the cpw line 120, the tapered shape and proximity of the signal line 122 to the ground element 124 will create a high intensity E-field between the tip of the tapered section 122a and the opposing section of the ground element 124. The high intensity E-field results in improved event detection sensitivity for the supplied sample. The illustrated taper is not exhaustive of the geometries possible and other shapes such as large angle bends, miters, curved shapes, or other structures may be used in alternative embodiments under the present invention. Any of the aforementioned sample containment structures or modifications thereof may be adapted for use with this biosensor 200.

Figure 3:
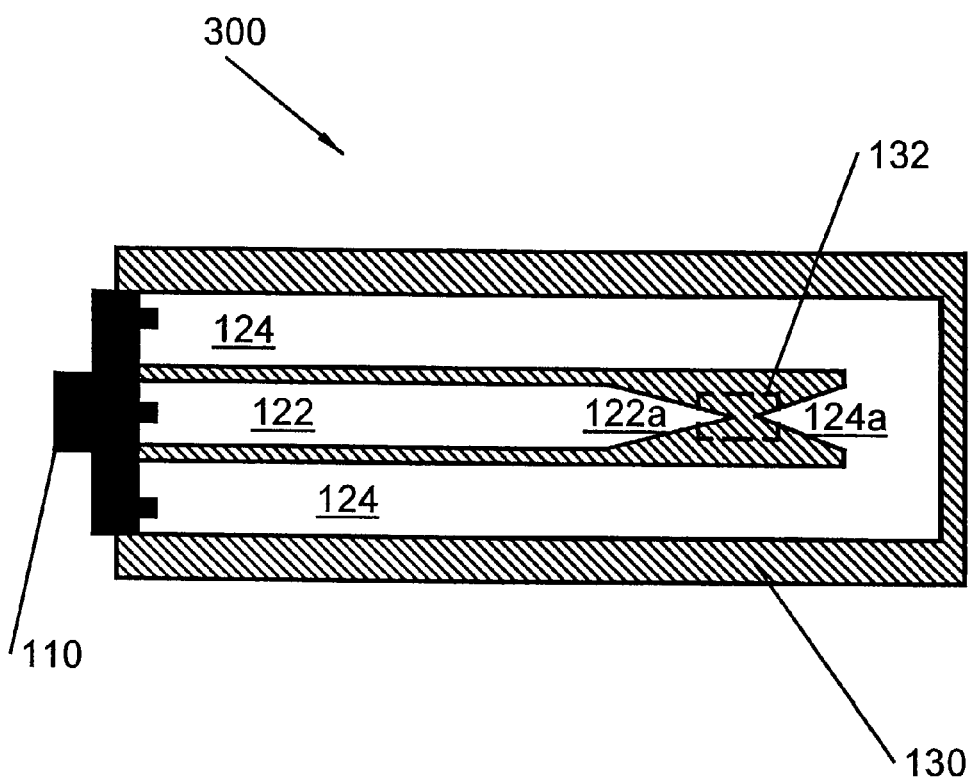
FIG. 3 illustrates a top view of a third embodiment of the coplanar waveguide biosensor in accordance with the present invention.

FIG. 3 illustrates top view of a third embodiment of the coplanar waveguide biosensor 300 in accordance with the present invention. As illustrated, both the signal line 122 and the ground element 124 includes tapered sections 122a and 124a, respectively, the area between them defining a detection region 132. By tapering both line sections, an even higher E-field intensity is created and greater event detection sensitivity achieved. The reader will appreciate that these are but a few of the various modification possible and other configurations are possible under alternative embodiments under the present invention. As above, any of the aforementioned sample containment structures or modifications thereof may be adapted for use with this biosensor.

Figure 4A:
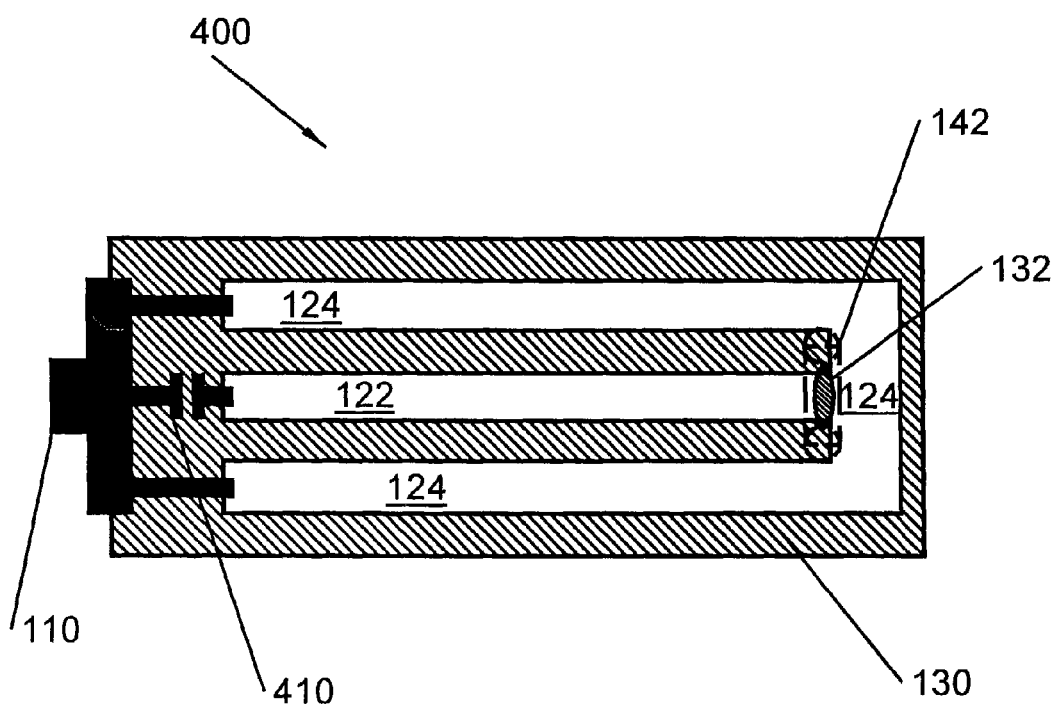
FIGS. 4a, 4b, 4c illustrates a top view of a fourth embodiment of the coplanar waveguide biosensor in accordance with the present invention.
Figure 4B:
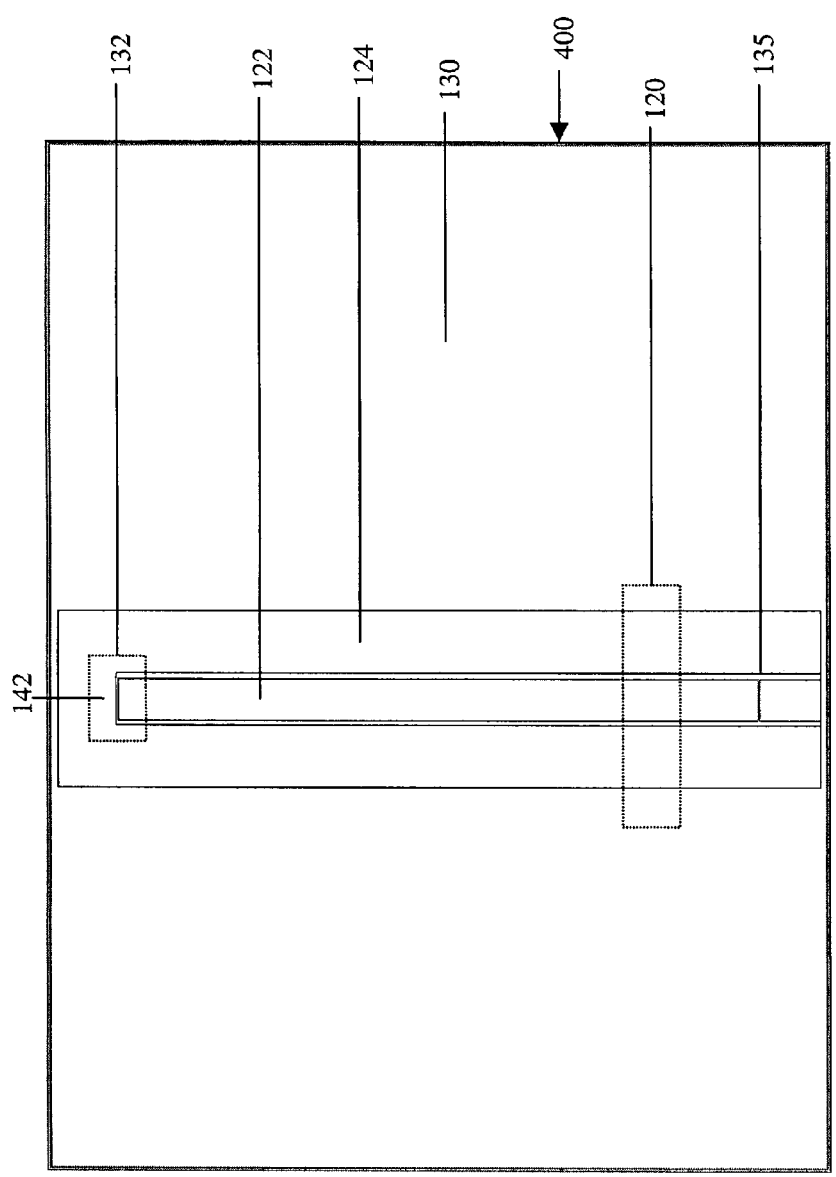
Figure 4C:
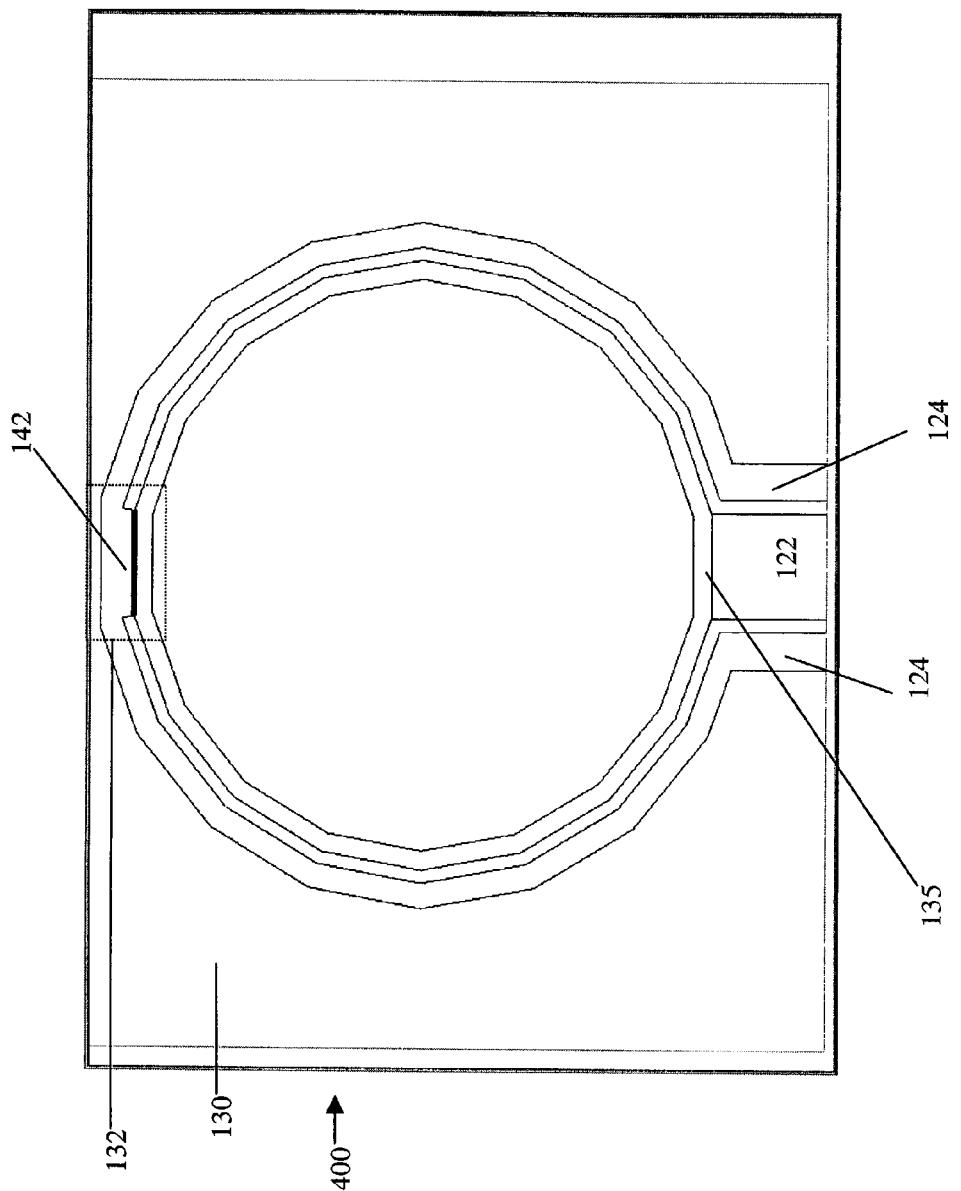

FIGS. 4a, 4b, and 4c illustrate a top view of a fourth embodiment of the coplanar waveguide biosensor 400 in accordance with the present invention. In this embodiment, the creation of a coplanar waveguide resonant circuit by the insertion of discontinuities in the signal line or ground elements is discussed. In FIG. 4a, the lead ground element 124 extends around the signal line 122 forming a small gap (not shown) there between at the terminus of the signal line 122. At its input, the signal line 122 is connected to a capacitor (preferably tunable) 410 that couples the signal line 122 to the coupling input or the connector 110. The unit 400 functions as a periodic resonant circuit, as known in the art of high frequency circuit design. Placing a discontinuity, in the form of a small gap, across the center conductor of a coplanar waveguide results in a gap-coupled coplanar waveguide (CPW) resonant circuit. The gap placed across the center conductor is equivalent to a series capacitor. This technique is described in detail for a microstrip line on page 334 of "Microwave Engineering", David M. Pozar 1998 John Wiley and Sons, Inc. Placing between the center conductor and ground plane a gap that is similarly sized to the series capacitive gap forms the detection region 132. The gap area that forms the detection region 132 is equivalent to a parallel capacitor. When a micro fluidic channel 142 carrying the event is brought into contact with the parallel capacitor, the molecular or cellular event is delivered to the detection region 132.

The biosensor 400 may take the form of any resonant circuit. A linear gap-coupled coplanar waveguide resonant circuit is shown in FIG. 4B, while a circular gap-coupled coplanar waveguide resonant circuit is shown in FIG. 4C. In the linear resonant circuit of FIG. 4b, a discontinuity in the form of a coupling gap 135 transforms the area of the center conductor 122 between the coupling gap 135 and the gap at the signal line terminus 132 (which forms the detection region) into a resonant circuit. A discontinuity in the form of coupling gap 135 transforms the circular shaped signal line 122 terminus into a resonant ring as shown in FIG. 4C. Passage of molecular or cellular event via a microfluidic channel 142 into contact with the detection region 132 allows detection of the event. The biosensor 400 may be achieved using one-port or multi-port coplanar waveguide resonant circuits on a dielectric substrate 130, and discontinuities may be created in both the signal line 122 and/or ground elements 124.

At frequencies where the length of the signal line 122 approaches $\lambda/2$ (or odd integer multiples thereof), the cpw line 120 (comprised of the signal line 122 and the ground elements 124) will resonate, thereby returning to the detection region 132 most of the incident signal reflected therefrom This mode of operation enhances the biosensor's sensitivity as the incident signal effectively makes multiple passes through the sample contained within the fluid channel 142. The capacitor 410 may be adjusted to tune the cpw line to a particular frequency. As above, any of the aforementioned sample containment structures or modifications thereof may be adapted for use with this biosensor.

Figure 5:
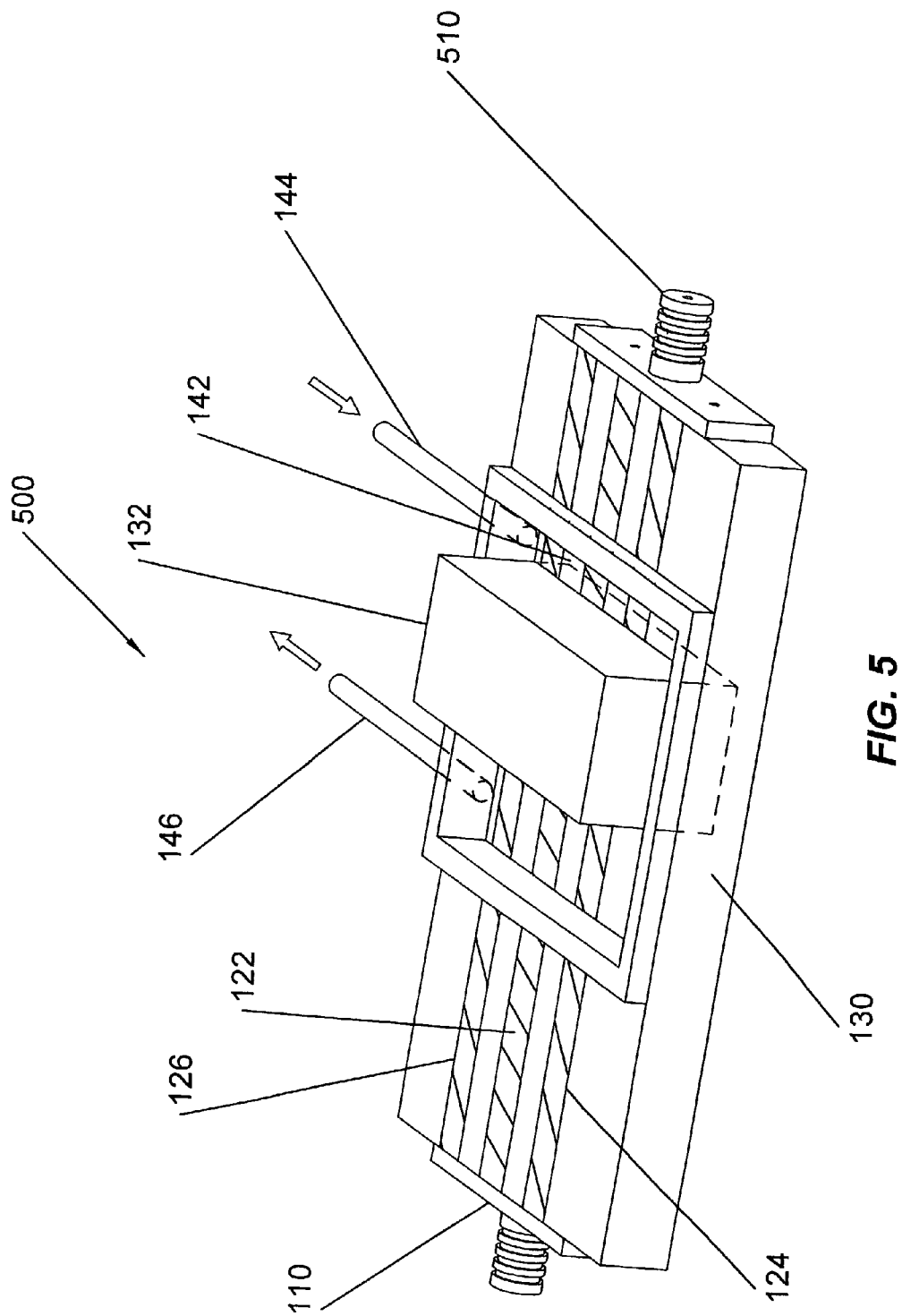
FIG. 5 illustrates a perspective view of a fifth embodiment of the coplanar waveguide biosensor in accordance with the present invention.

FIG. 5 illustrates top view of a fifth embodiment of the coplanar waveguide biosensor 500 in accordance with the present invention. This embodiment illustrates a two-port cpw line 120 electrically coupled between a first connecter 110 and a second connector 510. The sample containment structure 140 is a modified version of that shown in FIG. 1B, and includes a fluid channel 142 that extends laterally over the signal line 122 and both ground elements 124 and 126. The biosensor's detection region 132 also includes portions of both ground elements 124 and 126 and the signal line 122. The sample solution is communicated into and out of the fluid channel 142 via sample inlet and outlet ports 144 and 146. In a specific embodiment, the sample containment structure 140 is constructed from borosilicate glass and is thermally bonded to the dielectric substrate 130 (also borosilicate glass), although other materials and attachment techniques described herein or conventionally known may be used in alternative embodiments under the present invention. The two-port configuration advantageously provides both a reflection ($S_{11}$) measurement capability and an insertion loss ($S_{21}$) measurement capability for detecting molecular or cellular events occurring within the fluid channel 142.

While the above is a complete description of possible embodiments of the invention, various alternatives, modification and equivalents may be used to which the invention is equally applicable. For example, any of the illustrated biosensors may be used in an array configuration, such as those described in applicant's concurrently filed application entitled "Well-Based Biosensor for Detecting Molecular and Cellular Events," Ser. No. 09/929,520, herein incorporated by reference in its entirety for all purposes. Other modifications will be apparent to the reader as well in view of the references incorporated herein. Accordingly, the above description should be viewed as only a few possible embodiments of the present invention, the boundaries of which is appropriately defined by the metes and bounds of the following claims.

The following commonly owned applications and patents are concurrently filed herewith, and are incorporated by reference in their entirety for all purposes:

Ser. No. 09/929,513 entitled "Methods for Analyzing Cellular Events, filed Aug. 13, 2001; and "Well-Based Biosensor for Detecting Molecular or Cellular Events," Ser. No. 09/929,520.

U.S. Pat. No. 6,368,795 entitled "Method and Apparatus for Detecting Molecular Binding Events, filed Feb. 1, 1999 and issued Apr. 9, 2002;

U.S. Pat. No. 6,338,968 entitled "Method and Apparatus for Detecting Molecular Binding Events," filed Aug. 2, 1999 and issued Jan. 15, 2002;

U.S. Pat. No. 6,395,480 entitled "Computer Program and Database Structure for Detecting Molecular Binding Events," filed Feb. 1, 1999 and issued May 28, 2002;

U.S. Pat. No. 6,376,258 entitled "Resonant Bio-assay Device and Test System for Detecting Molecular Binding Events," filed Jan. 10, 2000 and issued Apr. 23, 2002;

U.S. Pat. No. 6,485,905 entitled "Test Systems and Sensors for Detecting Molecular Binding Events," filed Aug. 2, 1999 and issued Nov. 26, 2002;

U.S. Pat. No. 6,287,776 entitled "Methods of Nucleic Acid Analysis," filed Aug. 2, 1999 and issued Sep. 11, 2001;

U.S. Pat. No. 6,287,874 entitled "Methods for Analyzing Protein Binding Events," filed Aug. 2, 1999 and issued Sep. 11, 2001;

Ser. No. 09/687,456 entitled "System and method for detecting and identifying molecular events in a test sample," filed Oct. 13, 2000;

Ser. No. 60/248,298 entitled "System and method for real-time detection of molecular interactions," filed Nov. 13, 2000 (now abandoned);

Ser. No. 09/775,718 entitled "Bioassay device for detecting molecular events," filed Feb. 1, 2001 (abandoned);

U.S. Pat. No. 6,586,946 entitled "System and method for detecting and identifying molecular events in a test sample using a resonant test structure," filed Feb. 1, 2001 and issued Jul. 1, 2003;

Ser. No. 60/268,401 entitled "A system and method for characterizing the permittivity of molecular events," filed Feb. 12, 2001 (now abandoned);

Ser. No. 60/275,022 entitled "Method for detecting molecular binding events using permittivity," filed Mar. 12, 2001 (now abandoned);

Ser. No. 60/277,810 entitled "Bioassay device for Detecting Molecular Events," filed Mar. 21, 2001 (now abandoned);

U.S. Pat. No. 6,627,461 entitled "Method and Apparatus for Detection of Molecular Events Using Temperature Control of Detection Environment," filed Apr. 18, 2001 and issued Sep. 30, 2003; and Ser. No. 09/880,331 entitled "Reentrant Cavity Bioassay for Detecting Molecular or Cellular Events," filed Jun. 12, 2001; and U.S. Pat. No. 6,461,808 entitled "Pipette-Loaded Bioassay Assembly for Detecting Molecular or Cellular Events," filed Jun. 12, 2001 and issued Oct. 8, 2002.

What is claimed is:

1. A coplanar waveguide biosensor for detecting molecular or cellular events, comprising:
   a one-port coplanar waveguide transmission line operable to support the propagation of a electromagnetic test signal, comprising:
      a signal line configured to conduct a time-varying voltage therealong, wherein the signal line comprises a tapered section;
      and one or more ground elements configured to maintain a time-invariant voltage therealong, the one or more ground elements spaced apart from the signal line and located generally within the same plane as the signal line, wherein a detection region is formed between a portion of the signal line and a portion of at least one of the one or more ground elements; and
   a sample containment structure intersecting the detection region of the one-port coplanar waveguide transmission line, wherein the sample containment structure comprises a cavity operable to hold 1 ml or less of sample solution within the detection region.

2. The coplanar waveguide biosensor of claim 1, wherein the one or more ground elements comprises a tapered section.

3. The coplanar waveguide biosensor of claim 1, wherein the signal line comprises a tapered section and the one or more ground elements comprises a tapered section.

4. The coplanar waveguide biosensor of claim 1, wherein the coplanar waveguide transmission line comprises a resonant structure.

5. A method for detecting a molecular or cellular event using a coplanar waveguide, comprising:
   providing a coplanar waveguide transmission line operable to support the propagation of a electromagnetic test signal,
   the coplanar wave guide comprising:
      a signal line configured to conduct a time-varying voltage there along; and one or more ground elements configured to maintain a time-invariant voltage there along, the one or more ground elements spaced apart from the signal line and located generally within the same plane as the signal line, wherein a detection region is formed between a portion of the signal line and a portion of at least one of the one or more ground elements;
   providing a sample containment structure intersecting the detection region of the coplanar waveguide transmission line, wherein the sample containment structure comprises a cavity operable to hold 1 ml or less of sample solution within the detection region, wherein the sample containment structure comprises a fluid channel,
   propagating an incident test signal along the coplanar waveguide signal line to the detection region,
   electromagnetically coupling at least a portion of the incident test signal to the molecular or cellular event, and
   measuring the modulation of the incident test signal wherein the signal modulation is indicative of the presence and identity of the molecular event.

6. The method of claim 5, wherein the sample containment structure comprises a flow tube.

7. The method of claim 5, wherein the signal line comprises a tapered section.

8. The method of claim 5, wherein the one or more ground elements comprises a tapered section.

9. The method of claim 5, wherein the signal line comprises a tapered section and the one or more ground elements comprises a tapered section.

10. The method of claim 5, wherein the coplanar waveguide transmission line comprises a resonant structure.

11. The method of claim 5, further comprising providing at least one sample port operable to supply the sample solution to the cavity.

12. The method of claim 11, wherein the signal detector comprises a network analyzer.

13. The method of claim 11, wherein the signal detector comprises a vector voltmeter.

14. The method of claim 11, wherein the signal source is operable to output one or more signals from 300 KHz to 3 GHz.

15. The method of claim 11, wherein the signal source is operable to output one or more signals from 45 MHz to 26 GHz.

16. The method of claim 5, wherein the molecular event is directly or indirectly physically attached to the coplanar waveguide transmission line within the detection region.

17. The method of claim 5, wherein the molecular event is separated from the coplanar waveguide transmission line within the detection region.

18. The method of claim 5, wherein the cellular event is directly or indirectly physically attached to the coplanar waveguide transmission line within the detection region.

19. The method of claim 5, wherein the cellular event is separated from the coplanar waveguide transmission line within the detection region.

20. A method for detecting a molecular or cellular event using a coplanar waveguide, comprising:
   providing a signal source operable to output an electromagnetic test signal;
      providing a coplanar waveguide transmission line electrically coupled to the signal source and operable to support the propagation of a electromagnetic signal, the coplanar waveguide transmission line comprising:
      a signal line configured to conduct a time-varying voltage there along;
      and
   one or more ground elements configured to maintain a time-invariant voltage there along, the one or more ground elements spaced apart from the signal line and located generally within the same plane as the signal line, wherein a detection region is formed between a portion of the signal line and a portion of at least one of the one or more ground elements;
   providing a sample containment structure intersecting the detection region of the one-port coplanar waveguide transmission line, wherein the sample containment structure comprises a cavity operable to hold 1 ml or less of sample solution within the detection region,
   providing a signal detector electrically coupled to the coplanar waveguide signal line,
   propagating an incident test signal along the coplanar waveguide signal line to the detection region,
   electromagnetically coupling at least a portion of the incident test signal to the molecular or cellular event, and
   measuring the modulation of the incident test signal wherein the signal modulation is indicative of the presence and identity of the molecular event.

21. A coplanar waveguide biosensor for detecting molecular or cellular events, comprising:

a coplanar waveguide transmission line operable to support the propagation of a electromagnetic test signal, comprising:
  a signal line configured to conduct a time-varying voltage there along, the signal line comprising a tapered section; and one or more ground elements configured to maintain a time-invariant voltage therealong, the one or more ground elements spaced apart from the signal line and located generally within the same plane as the signal line, wherein a detection region is formed between a portion of the signal line and a portion of at least one of the one or more ground elements; and
a sample containment structure intersecting the detection region of the one-port coplanar waveguide transmission line, wherein the sample containment structure comprises a cavity operable to hold 1 ml or less of sample solution within the detection region.

22. A coplanar waveguide biosensor for detecting molecular or cellular events, comprising:
  a coplanar waveguide transmission line operable to support the propagation of a electromagnetic test signal, comprising:
    a signal line configured to conduct a time-varying voltage there along; and
one or more ground elements configured to maintain a time-invariant voltage therealong, the one or more ground elements spaced apart from the signal line and located generally within the same plane as the signal line, wherein a detection region is formed between a portion of the signal line and a portion of at least one of the one or more ground elements, the one or more ground elements comprising a tapered section; and
a sample containment structure intersecting the detection region of the one-port coplanar waveguide transmission line, wherein the sample containment structure comprises a cavity operable to hold 1 ml or less of sample solution within the detection region.

23. A coplanar waveguide biosensor for detecting molecular or cellular events, comprising:
  a coplanar waveguide transmission line operable to support the propagation of a electromagnetic test signal, comprising:
    a signal line configured to conduct a time-varying voltage there along, the signal line comprising a tapered section; and
one or more ground elements configured to maintain a time-invariant voltage therealong, the one or more ground elements spaced apart from the signal line and located generally within the same plane as the signal line, wherein a detection region is formed between a portion of the signal line and a portion of at least one of the one or more ground elements, the one or more ground elements comprising a tapered section; and
a sample containment structure intersecting the detection region of the one-port coplanar waveguide transmission line, wherein the sample containment structure comprises a cavity operable to hold 1 ml or less of sample solution within the detection region.

24. A coplanar waveguide biosensor for detecting molecular or cellular events, comprising:
  a coplanar waveguide transmission line comprising a resonant structure and operable to support the propagation of a electromagnetic test signal, comprising:
    a signal line configured to conduct a time-varying voltage there along; and
one or more ground elements configured to maintain a time-invariant voltage therealong, the one or more ground elements spaced apart from the signal line and located generally within the same plane as the signal line, wherein a detection region is formed between a portion of the signal line and a portion of at least one of the one or more ground elements; and
a sample containment structure intersecting the detection region of the one-port coplanar waveguide transmission line, wherein the sample containment structure comprises a cavity operable to hold 1 ml or less of sample solution within the detection region.

25. A method for detecting a molecular or celluar event using a coplanar waveguide, comprising:
  providing a coplanar waveguide transmission line operable to support the propagation of an electromagnetic test signal,
  the coplanar wave guide comprising a resonant structure,
  a signal line configured to conduct a time-varying voltage there along, and
one or more ground elements configured to maintain a time-invariant voltage therealong, the one or more ground elements spaced apart from the signal line and located generally within the same plane as the signal line, wherein a detection region is formed between a portion of the signal line and a portion of at least one of the one or more ground elements;
providing a sample containment structure intersecting the detection region of the one-port coplanar waveguide transmission line, wherein the sample containment structure comprises a cavity operable to hold 1 ml or less of sample solution within the detection region,
propagating an incident test signal along the coplanar waveguide signal line to the detection region,
electromagnetically coupling at least a portion of the incident test signal to the molecular or cellular event, and
measuring the modulation of the incident test signal wherein the signal modulation is indicative of the presence and identity of the molecular event.

* * * * *